(12) United States Patent
Kumpe et al.

(10) Patent No.: US 7,625,866 B2
(45) Date of Patent: Dec. 1, 2009

(54) CONCENTRATE OF A FACTOR VIII:C-CONTAINING VON WILLEBRAND FACTOR AND THE PROCESS RELATING THERETO

(75) Inventors: Gerhardt Kumpe, Wetter (DE); Manfred Juraschek, Weimar (DE); Natascha Mayer, Marburg (DE); Stefan Schulte, Marburg (DE); Wilfried Wormsbächer, Kirchhain (DE)

(73) Assignee: CSL Behring GmbH, Marburg (DE)

( * ) Notice: Subject to any disclaimer, the term of this patent is extended or adjusted under 35 U.S.C. 154(b) by 0 days.

(21) Appl. No.: 10/670,563

(22) Filed: Sep. 26, 2003

(65) Prior Publication Data

US 2004/0132654 A1 Jul. 8, 2004

(30) Foreign Application Priority Data

Oct. 1, 2002 (DE) .............................. 102 46 125

(51) Int. Cl.
*A61K 38/37* (2006.01)
(52) U.S. Cl. .............................. 514/12; 514/2; 530/350; 530/383
(58) Field of Classification Search .................. 514/12, 514/2; 530/350, 383
See application file for complete search history.

(56) References Cited

U.S. PATENT DOCUMENTS

| 5,288,853 | A | 2/1994 | Bhattacharva et al. | |
|---|---|---|---|---|
| 6,228,613 | B1 | 5/2001 | Fischer et al. | |
| 6,239,261 | B1 * | 5/2001 | Heimburger et al. | 530/412 |
| 6,579,723 | B1 | 6/2003 | Mitterer et al. | |

FOREIGN PATENT DOCUMENTS

| JP | 0 705 846 A1 | 9/1995 |
|---|---|---|
| WO | WO 98/38218 | 9/1998 |

OTHER PUBLICATIONS

Heimburger et al., Drug Res. 31(1), Nr. 4 (1981), Faktor-Konzentrat, hochgereinigt und in Losung erhitzt, pp. 619-622.*
German Translation of Heimburger et al., pp. 1-14.*
Von N. Heimburger et al., "Factor VII-Konzentrat, hochgereinigt und in Lösung erhitzt", Arzneim-Forsch./Drug Res. 31 (I), Nr. 4, pp. 619-622, (1981).
Mannucci, P. M. et al., "Multicenter Comparison of von Willebrand Factor Multimer Sizing Techniques," *Thrombosis and Haemostasis*, 54(4): 873-876 (1985).
Lombardi, R. et al., "Electroblot and Immunoperoxidase Staining for Rapid Screening of the Abnormalities of the Multimeric Structure of von Willebrand Factor in von Willebrand's Disease," *Thrombosis and Haemostasis*, 55(2): 246-249 (1986).
Baillod, P. et al., "Multimeric Analysis of von Willebrand Factor by Vertical Sodium Dodecyl Sulphate Agarose Gel Electrophoresis, Vacuum Blotting Technology and Sensitive Visualization by Alkaline Phosphatase Anti-Alkaline Phosphatase Complex," *Thrombosis Research*, 66: 745-755 (1992).
Girma, J.P. et al., "Structure-Function Relationship of Human Von Willebrand Factor," *Blood*, 70(3): 605-611 (1987).
Hamer, R. J., "Factor VIII Binds to von Willebrand Factor Via Its $M^r$-80 000 Light Chain," *Eur. J. Biochem.*, 166: 37-43 (1987).
Cornu, P. et al., "Transfusion Studies in von Willebrand's Disease: Effect on Bleeding Time and Factor VIII," *Brit. J. Haemat*, 9: 189-202 (1963).
Weiss, H. J. et al., "Stabilization of Factor VIII in Plasma by the von Willebrand Factor," *The Journal of Clinical Investigation*, 60: 390-404 (1977).
Jaffe, E. A. et al., "Synthesis of von Willebrand Factor by Cultured Human Endothelial Cells," *Proc. Nat. Acad. Sci*, 71(5): 1906-1909 (1974).
Nachman, R. et al., "Synthesis of Factor VIII Antigen by Cultured Guinea Pig Megakaryocytes," *The Journal of Clinical Investigation*, 60: 914-921 (1977).
Scott, J. P. et al., "Therapy of von Willebrand Disease," *Seminars in Thrombosis and Hemostasis*, 19(1): 37-47 (1993).
Perret, B.A. et al., "Isolation of Small Molecular Forms of Factor VIII/von Willebrand Factor from Plasma," *Haemostasis*, 14: 289-295 (1984).
Kasper, C.K. et.al.; "A More Uniform Measurement of Factor VIII Inhibitors," *Thrombos. Diathes. Haemorrh.*, 34: 869-872 (1975).
Behrmann, M. et al., "Von Willebrand Factor Modulates Factor VIII Immunogenicity: Comparative Study of Different Factor VIII Concentrates in a Haemophilia A Mouse Model," *Thromb Haemost*, 88: 221-229 (2002).

* cited by examiner

*Primary Examiner*—Chih-Min Kam
(74) *Attorney, Agent, or Firm*—Finnegan, Henderson, Farabow, Garrett & Dunner, L.L.P.

(57) ABSTRACT

The invention relates to a concentrate and a process for producing a factor VIII:C-containing von Willebrand factor by fractional precipitation from a liquid comprising factor VIII:C and von Willebrand factor, resulting in an increased content of high molecular weight multimers of von Willebrand factor and a ratio of the vWF:RCoF activity to vWF:Ag of greater than 1.

11 Claims, No Drawings

CONCENTRATE OF A FACTOR VIII:C-CONTAINING VON WILLEBRAND FACTOR AND THE PROCESS RELATING THERETO

The invention relates to a concentrate of a factor VIII:C-containing von Willebrand factor which has therapeutic advantages because of its particular composition.

Functional von Willebrand factor (vWF), a glycoprotein, circulates in the bloodstream with varying molecular weight distribution, the so-called multimers, and the multimers may have a molecular weight distribution of from 500 kilodalton (kd) up to 20 000 kd. The smallest unit therein is the dimer with a molecular weight of about 550 kd; it consists of two monomers which are connected together by disulfide bridges. Further disulfide linkages of these dimers result in polymers, so-called multimers, with a molecular weight of up to 20 000 kd. The molecular weight distribution of von Willebrand multimers can be determined both quantitatively and qualitatively by agarose gel electrophoresis (ref. 1, 2, 3). The physiological function of von Willebrand factor is its property of adhering to injured endothelium and of aggregating platelets (ref. 4). This results, in so-called primary hemostasis, initially in the formation of a platelet plug and thus initial stoppage of bleeding; subsequently the coagulation cascade takes place, so-called secondary hemostasis, and finally wound closure.

A further important function of von Willebrand factor is its ability to form complexes with factor VIII:C (FVIII:C); this complex formation with vWF protects FVIII:C in the plasma from proteolytic degradation. In a healthy organism there is always a sufficiently high level of FVIII:C present in the complex with vWF. It is assumed in this connection that the two proteins FVIII:C and vWF are connected by a noncovalent linkage between the N terminus of the light chain of FVIII:C and the N terminus of the vWF subunit (ref. 5, 6).

Associations of this type were observable for example on use of cryoprecipitate from the plasma of healthy donors for replacement in von Willebrand patients. Replacement with normal cryoprecipitate induced an increase in FVIII:C lasting several hours in patients. The decrease took place slowly with the half-life of vWF.

Antihemophilic factor, the factor VIII coagulation protein (FVIII:C), circulates in the plasma together with the vWF as noncovalently linked complex, and preparative breaking up of the vWF/FVIII:C complex is possible only with difficulty. It was for a long time not known that vWF and FVIII:C are two different proteins which are also synthesized at different places in the body: FVIII:C in the liver and vWF in endothelial cells and megakaryocytes (ref. 9, 10).

The absence of vWF or even just a reduction thereof results in a prolonged bleeding time and a serious tendency to bleeding; the pathological state is called von Willebrand syndrome and may be manifested in several forms. These range from an abnormal size distribution of the vWF multimers up to partial or complete absence of a functional von Willebrand factor, called type III von Willebrand syndrome. In these cases it is possible for both the high molecular weight and the low molecular weight multimers to be diminished or even completely absent. von Willebrand syndrome (e.g. type III) results in a deficiency in FVIII:C and thus in hemophilia A, because FVIII:C is protected in a complex with vWF and, without this, is degraded proteolytically in the plasma within a very short time.

On use of normal cryoprecipitate for replacement in a hemophilia patient there is observed to be only a rapid and brief increase in measurable FVIII:C activity (ref. 7, 8). However, on use of plasma or cryoprecipitate from a hemophiliac donor for replacement in a von Willebrand patient, paradoxically there is also a measurable increase in FVIII. This can be explained by the stabilization by vWF. The von Willebrand patient synthesizes FVIII which is, however, continuously cleaved proteolytically in the plasma after release.

vWF is of great importance together with FVIII:C for normal coagulation. The plasma concentration of vWF is about 10 μg/ml. FVIII:C represents a much smaller protein content in terms of mass, about 0.2 μg/ml.

As mentioned at the outset, vWF mediates platelet aggregation and thus primary hemostasis at the injured vessels. Together with other procoagulant factors such as the so-called contact factors, FVIII:C, phospholipids and calcium, further coagulation takes place via activation of factor VIII until fibrin is formed and the wound is closed (ref. 11).

The vWF/FVIII:C complex can be separated only with difficulty, which is why FVIII:C is found together with vWF in cryoprecipitate and, in gel filtrations, elutes together with vWF in the void volume (ref. 12).

The process frequently employed in the plasma industry for concentrating vWF/FVIII:C is that of cryo-precipitation. In this, an insoluble precipitate (cryoprecipitate) is obtained by controlled thawing of deep-frozen plasma. Removal of this precipitate results not only in the cryoprecipitate but also the so-called cryo-poor plasma. The cryoprecipitate contains concentrated vWF/FVIII:C complex together with some of the plasma proteins fibrinogen and fibronectin. The vWF multimer spectrum in cryoprecipitate comprises an effective composition of the multimers compared with that in normal plasma. It is mainly the higher molecular weight multimers which precipitate in this process, with virtually all the high molecular weight vWF multimers from plasma being recovered in cryoprecipitate. About 20% of the vWF, which shows no measurable activity, remains together with FVIII:C in the cryo-poor plasma.

Pooled plasma from healthy people contains "by definition" 1 IU/ml functional activity based on all coagulation factors. The functional activity of vWF is usually measured by the ristocetin-mediated platelet aggregation which correlates with the concentration of intact vWF. This is described as the vWF ristocetin cofactor activity (vWF:RCoF) with concentrations stated in IU/ml. The associated protein is referred to as vWF antigen, abbreviated to vWF:Ag.

In cases of severe von Willebrand disease, replacement using a vWF concentrate having a high functional content of FVIII:C is of considerable advantage; on the one hand, the bound procoagulant factor VIII:C is a measure of the binding capacity and indicates an intact vWF, and on the other hand the presence of FVIII:C leads to a significant shortening of the bleeding time. Without FVIII:C it would be necessary in the treatment of von Willebrand diseases by replacement to administer in addition FVIII:C products. The precondition for rapid efficacy in von Willebrand diseases is thus a vWF with normal factor FVIII:C binding capacity, advantageously enriched with a high molecular weight vWF multimer content and a content of intact factor VIII:C.

European patent application EP 0 705 846 (ref. 13) describes a preparative process for separating von Willebrand factor into a higher molecular weight fraction and a lower molecular weight fraction of vWF. This separation is achieved by the vWF being bound to an affinity support and then being eluted therefrom at a different salt concentration. It is possible in this way to obtain high molecular weight vWF fractions which have a particularly high physiological activity.

Chromatographic processes for fractionating vWF into higher molecular weight and lower molecular weight multimers have already been disclosed. However, it was not possible in these cases to obtain specifically optimal vWF/FVIII:C complexes with enriched high molecular weight vWF multimers.

It is also known that FVIII:C, whether recombinant or plasma FVIII, may on repeated administration and in higher concentrations, dissociated from von Willebrand factor, lead to unwanted immune responses since antibody production may be induced to different extents depending on the mode of preparation and purity. These antibodies, called hemophilia A inhibitors or FVIII:C inhibitors, which can be determined quantitatively in "Bethesda units" as disclosed in a publication: Thrombos. Diathes haemorrh. (Stuttg.), 1975, 34, 869 (ref. 14), lead to unwanted side effects and, where appropriate, to hemorrhages.

If these FVIII:C products are preincubated with multimeric von Willebrand factor, the production of these anti-FVIII immunoglobulins is substantially prevented, and relatively large quantities can be used repeatedly without the need to worry about these side effects. The product of the invention thus has a significant advantage on use. This association has been demonstrated in a mouse model of hemophilia (ref. 15).

The invention disclosed in this application is based on the problem of producing a concentrate of a factor VIII:C-containing von Willebrand factor which comprises enriched high molecular weight vWF multimers and has a ratio of the vWF:RCoF activity to vWF:Ag of greater than 1.

The problem described above is solved by the concentrate disclosed herein. This concentrate is obtained by fractional precipitation from a liquid comprising factor VIII:C and von Willebrand factor and has an increased content of high molecular weight multimers of von Willebrand factor and a ratio of the vWF:RCoF activity to vWF:Ag of greater than 1.

The advantages achieved with the invention are that it is possible to provide a concentrate of a factor VIII:C-containing von Willebrand factor which can be obtained by a simple preparative fractional precipitation from a liquid comprising factor VIII:C and von Willebrand factor, with the concentrate having an increased content of high molecular weight multimers of von Willebrand factor and a ratio of the vWF:RCoF activity to vWF:Ag of greater than 1. The concentrate obtained in this way is suitable for replacement in cases of serious von Willebrand disease; the presence of factor VIII:C is of considerable importance in this connection, since the bound procoagulant factor VIII:C is stabilized by vWF and thus leads to a significant shortening of the bleeding time. The high content of high molecular weight multimers is an essential precondition for its rapid efficacy.

Further advantageous embodiments of the invention are indicated in the Examples portion of this specification.

The concentrate of the invention can be obtained from human plasma, a plasma fraction such as, for example, cryoprecipitate or from genetically modified cell material. The preferred starting material therefor is human cryoprecipitate which comprises the vWF-FVIII:C complex in addition to the plasma proteins fibrinogen and fibronectin. This cryoprecipitate is obtained from deep-frozen citrated plasma which is converted by controlled heating (equilibration) into the liquid state, where, at temperatures between 0 and +2° C., part of the fibrinogen, of the fibronectin and the VWF:FVIII:C complex remain behind as precipitate and can be removed for example by centrifugation. The cryoprecipitate obtained in this way can be temporarily stored deep-frozen and serves as starting material for obtaining the purified vWF/FVIII:C complex.

The concentrate of the invention is preferably obtained by fractional precipitation using amino acids, especially using glycine, and an alkali metal or alkaline earth metal salt, preferably sodium chloride. This entails glycine being added to a stirred aqueous solution of cryoprecipitate until fibrinogen has very substantially precipitated from the solution. The precipitated fibrinogen residue is then removed by centrifugation. The vWF/FVIII:C complex is precipitated from the supernatant by adding an alkali metal or alkaline earth metal salt, in a preferred embodiment by adding sodium chloride, with stirring, and is removed by centrifugation. The vWF/FVIII:C-containing precipitate obtained in this way is dissolved with an isotonic buffer, stabilized with sucrose and glycine and then pasteurized.

It is particularly advantageous to carry out the precipitation of the vWF/FVIII:C-containing precipitate with concentrations of from 70 to 160 g/l glycine and from 100 to 160 g/l sodium chloride. It is possible by this adjustment of a concentration range to shift the activity/ratio in favor of a higher vWF:RCoF activity, which is associated with an enrichment of high molecular weight vWF multimers. Also suitable for the precipitation besides glycine are other physiological or even nonphysiological amino acids, such as α-alanine, α-, β- or γ-aminobutyric acid, lysine, valine, asparagine and glutamic acid, and substances of similar chemical structure. Thus, for example, a precipitation is likewise obtained with β-alanine in a similar manner to glycine.

The adjustment of a particular concentration range of precipitants, for example amino acids, preferably glycine, with a suitable ionic strength in a range from 5 to 30 percent by weight of salts from the alkali metal and alkaline earth metal groups, preferably sodium chloride, makes it possible to shift the activity ratio in favor of a higher vWF:RCoF activity, this being the result of enrichment of high molecular weight vWF multimers. A key role is played in this by the concentration of glycine, to which this invention also relates.

The process of the invention is expediently carried out in such a way that initially the dissolved cryoprecipitate is mixed with an aluminum hydroxide suspension to adsorb the prothrombin complex which is trapped in small quantities, followed by stirring and removal. The supernatant then contains the factor VIII:C and von Willebrand factor, which are obtained by fractional precipitation.

The cryoprecipitate is dissolved in an isotonic buffer by stirring and gentle heating so that a protein concentration of from 2 to 3% is obtained. The crude cryo solution obtained in this way is then mixed with an aluminum hydroxide suspension to adsorb the prothrombin complex factors, and the remaining prothrombin factors are adsorbed while stirring and are removed together with the Al(OH)$_3$ pellet. After removal of the prothrombin complex factors, the cryo solution can be subjected to a virus inactivation by pasteurization or with acridine or acridine derivatives in compliance with DE 44 44 045 and be stabilized, for which purpose calcium ions are particularly suitable.

Subsequently, glycine is added with stirring to the cryo solution obtained after the virus inactivation, and the fibrinogen is precipitated and removed by centrifugation. NaCl is subsequently added with stirring to the resulting supernatant, and thus the vWF/FVIII:C is precipitated and is removed by subsequent centrifugation. The resulting vWF/FVIII:C-containing precipitate is dissolved in an isotonic buffer, stabilized with sucrose and glycine and then heated at 60° C. for 10 hours. After pasteurization has taken place, the resulting solution serves as starting material for obtaining the vWF/FVIII:C complex with enriched high molecular weight multimer content.

Exemplary embodiments of the inventions are described in examples 1 to 6.

EXAMPLE 1

Dissolving of Cryoprecipitate, Al(OH)$_3$ Adsorption and Fibrinogen Removal 200 g of cryoprecipitate were dissolved broken up in 800 ml with a 0.1M NaCl/glycine solution. The cryo solution was mixed with 10% by volume of a 1.5% strength Al(OH)$_3$ suspension, stirred for 15 min and centrifuged. The removed Al(OH)$_3$ pellet was discarded. Glycine was added to the stirred Al(OH)$_3$ supernatant (820 ml) until the fibrinogen was deposited from the solution. The precipitate was centrifuged and the vWF/FVIII:C complex-containing supernatant was processed further.

vWF/FVIII:C Complex Precipitation, Dissolving, Stabilization, Pasteurization

15% NaCl was added to the stirred glycine-containing supernatant, and the vWF/FVIII:C complex was precipitated quantitatively. The precipitate was dissolved in 64 ml of NaCl/glycine buffer, stabilized with sucrose (1 g/ml) and glycine (150 g/l) and pasteurized at 60° C. for 10 h. After cooling, the pasteurized solution was diluted with the same volume of glycine/NaCl buffer.

Precipitation of the vWF/FVIII:C Fraction with Increased Content of High Molecular Weight Multimers 0.75 Parts of a precipitating medium was added in each case with stirring to the diluted solution (220 ml), which contained 1.6 g/l NaCl and 124.4 g/l glycine, in three batches a, b, c, so that the glycine content in the precipitation batch a) was 80 g/l
b) was 90 g/l
c) was 100 g/l, and the final concentration of NaCl reached 122 g/l in all cases. This resulted in each case in a fine precipitate, which was centrifuged after stirring for about 45 min. The fraction (44 ml in each case) dissolved in an isotonic buffer then contained the vWF and FVIII:C, enriched with high molecular weight multimers, as indicated by numerical ratios in table 1 below. Analysis for vWF:RCoF activity, vWF:Ag and FVIII:C resulted in the following ratio:

TABLE 1

FVIII:C, vWF:RCoF, vWF:Ag ratios from the batches of example 1.

|  | FVIII:C to vWF:RCoF | FVIII:C to vWF:Ag | vWF:Ag to vWF:RCoF |
|---|---|---|---|
| Starting material: | 1:3.1 | 1:2.5 | 1:1.2 |
| Batch a) | 1:2.4 | 1:0.7 | 1:3.6 |
| Batch b) | 1:3.1 | 1:1.3 | 1:2.4 |
| Batch c) | 1:3.5 | 1:1.8 | 1:2.4 |
| Cryo solution from Al (OH)$_3$Ads. (reference) | 1:1.6 | 1:2.6 | 1:0.6 |

Table 1 shows that the ratio of vWF:Ag to vWF:RCoF in the starting material was close to 1. In batch a) to c), the ratio was up to tripled in favor of vWF:RCoF activity compared with vWF:Ag.

EXAMPLE 2

Starting material for obtaining a fraction with enriched high molecular weight multimers was in this case a prefractionated, pasteurized vWF:FVIII:C-containing solution obtained from cryoprecipitate. The solution was clear and homogeneous and contained at this stage of the process 1.6 g/l NaCl and 124.4 g/l glycine.

To precipitate a first precipitate of the vWF/FVIII:C complex, according to the invention the NaCl/glycine equilibrium was adjusted by adding a precipitating medium adapted in each case in several batches so that the high molecular weight vWF multimers preferentially precipitated, which could be checked by the ratio of the concentrations of the vWF:RCoF activity to vWF:Ag and was distinctly greater than 1.

After the first precipitate had been centrifuged, the glycine concentration in the supernatant was increased in each case (second precipitation) and the vWF remaining in the supernatant was also precipitated. The high molecular weight content in this second precipitate was distinctly reduced, which was evident from the decrease in the ratio of the vWF:RCoF activity to the antigen concentration.

Description of 3 Precipitation Batches A, B, C:

0.75 times the volume of a precipitating medium (150 ml) was added in each case to 200 ml of starting material, stirring until addition was complete. A fine precipitate was produced and was centrifuged.

200 ml of vWF/FVIII:C-containing starting material already contained the following concentrations of NaCl and glycine:

1.6 g/l NaCl, 124.4 g/l glycine:

To attain the 1st precipitate, the precipitating media had the following concentrations of NaCl and glycine:

Precipitating medium for batch A: 283 g/l NaCl no glycine
Precipitating medium for batch B: 283 g/l NaCl 45 g/l glycine
Precipitating medium for batch C: 283 g/l NaCl 90 g/l glycine 150 ml of corresponding precipitating medium were added to 200 ml of starting material in each of batch A to C, resulting in the following final concentrations of NaCl and glycine in the particular precipitation batch:

|  | NaCl | Glycine |
|---|---|---|
| Batch A | 122.2 g/l | 71.1 g/l |
| Batch B | 122.2 g/l | 90.4 g/l |
| Batch C | 122.2 g/l | 109.6 g/l |

The resulting precipitates were removed and dissolved. The vWF:RCoF, vWF:Ag and FVIII:C concentrations were determined for the dissolved precipitates (~42 ml) and have been shown in table 2 below.

TABLE 2

|  | FVIII:C [IU/ml] | vWF:RCoF [IU/ml] | vWF:Ag [IU/ml] |
|---|---|---|---|
| Starting material | 14.7 | 39.8 | 35.0 |
| Batch A | 11.2 | 24.2 | 8.2 |
| Batch B | 44.7 | 138.7 | 87.2 |
| Batch C | 46.3 | 150.3 | 113.7 |

The respective ratio of the activities was calculated from table 2 and has been shown in table 3.

TABLE 3

FVIII:C, vWF:RCoF, vWF:Ag ratio from the batches of example 2

|  | FVIII:C to vWF:RCoF | FVIII:C to vWF:Ag | vWF:Ag to vWF:RCoF |
|---|---|---|---|
| Starting material: | 1:2.7 | 1:2.4 | 1:1.1 |
| Batch A | 1:2.2 | 1:0.7 | 1:3.0 |
| Batch B | 1:3.1 | 1:2.0 | 1:1.6 |
| Batch C | 1:3.5 | 1:2.5 | 1:1.3 |

The ratio of vWF:Ag to vWF:RCoF activity attained in batches A to C was shifted in favor of the vWF:RCoF activity compared with the starting material, meaning an increase in the high molecular weight multimers.

Precipitate or Second Precipitation from the Supernatants of Batches A to C:

Glycine was added to the supernatants of batches A to C while stirring in such a way that all 3 batches reached a glycine concentration of 160 g/l in each case. The resulting precipitates were centrifuged and dissolved. Determination of vWF:RCoF, vWF:Ag and FVIII:C concentration was followed by calculation of the numerical ratios. The ratio has been shown in table 4.

TABLE 4

FVIII:C, vWF:RCoF, vWF:Ag ratios from the batches of example 2

|  | FVIII:C to vWF:RCoF | FVIII:C to vWF:Ag | vWF:Ag to vWF:RCoF |
|---|---|---|---|
| Second precipitation of batch A | 1:4.5 | 1:3.7 | 1:1.1 |
| Second precipitation of batch B | 1:7.65 | 1:12.1 | 1:0.63 |
| Second precipitation of batch C | 1:5.9 | 1:15.4 | 1:0.26 |

The second precipitations depicted in table 4 showed in the vWF:Ag to vWF:RCoF ratio a distinct reduction in the vWF:RCoF activity, indicating a reduced quantity of high molecular weight multimers and thus also a reduction in the vWF functionality.

EXAMPLE 3

As in example 2, a prefractionated and pasteurized vWF and FVIII:C-containing completely clear solution containing, at this stage of the preparation, 1.6 g/l NaCl and 124.4 g/l glycine was employed. In 4 precipitation batches with the same NaCl/glycine concentration in each case the addition and incubation time was varied.

The glycine concentration was higher in the precipitation batch compared with example 1 and example 2; precipitation batches 1 to 4 differed only in the addition and incubation times in order to establish and to prove that the vWF:Ag/vWF:RCoF ratio resulting in the precipitation depended not on the exposure times but primarily on the glycine concentration.

In each of batches 1 to 4, 150 ml of precipitating medium which contained 283.01 g/l NaCl and 133.58 g/l glycine were added in each case to 200 ml of starting material with stirring. The variables were the addition and incubation times, NaCl and glycine concentration were the same for all batches, as is evident from table 5.

TABLE 5

Addition and incubation times in the precipitation batch of example 3.

|  | Addition [min] | Incubation [min] | NaCl conc. [g/l] | Glycine conc. [g/l] |
|---|---|---|---|---|
| Batch 1: | 120 | 30 | 122.2 | 128.3 |
| Batch 2: | 60 | 60 | 122.2 | 128.3 |
| Batch 3: | 60 | 90 | 122.2 | 128.3 |
| Batch 4: | 60 | 240 | 122.2 | 128.3 |

The resulting precipitates were centrifuged and dissolved. The supernatant from batch 1 was adjusted with further crystalline glycine to a concentration of 160 g/l and stirred for 2 h. The resulting precipitate was likewise dissolved. The FVIII:C, vWF:RCoF and vWF:Ag activity contents were measured and the ratio to one another was calculated. They are shown in table 6.

TABLE 6

FVIII:C, vWF:RCoF, vWF:Ag ratios from the batches of example 3; FVIII:C, vWF:RCoF, vWF:Ag ratios.

|  | FVIII:C to vWF:RCoF | FVIII:C to vWF:Ag | vWF:Ag to vWF:RCoF |
|---|---|---|---|
| Batch 1 | 1:2.4 | 1:2.7 | 1:0.9 |
| Second precipitation glycine from batch 1 | 1:1.4 | 1:5.3 | 1:0.3 |
| Batch 2 | 1:2.1 | 1:2.9 | 1:0.7 |
| Batch 3 | 1:2.3 | 1:2.7 | 1:0.9 |
| Batch 4 | 1:2.3 | 1:3.0 | 1:0.8 |

It emerged in this case that batches 1 to 4 were virtually comparable in the ratios of the measured activities despite different addition and incubation times. The NaCl concentration and the glycine concentration was the same in all 4 batches.

Only the second precipitation of batch 1 differed distinctly: the vWF ristocetin cofactor content was distinctly reduced, and the vWF:Ag content was greatly increased. The high molecular weight multimers were clearly absent from the dissolved second precipitation (not depicted).

EXAMPLE 4

The starting material in this case was likewise a prepurified vWF/FVIII:C fraction which contained 1.6 g/l NaCl and 124.4 g/l glycine.

Batch 1: In this case, 150 ml of precipitating medium which contained 283.01 g/l NaCl and 133.5 g/l glycine were added to 200 ml of starting material while stirring. Stirring was continued until the precipitation was complete, and then the precipitate was centrifuged and dissolved, and the activity was measured.

Batch 1a: Further glycine was added (second precipitation) to the remaining supernatant while stirring until the concentration reached 160 g/l, the precipitate from the second precipitation was centrifuged and dissolved, and the activity was measured as for batch 1.

Batch 2: 1 part of another precipitating medium which contained 300 g/l NaCl and no glycine was added to 1 part of the same starting material. After addition was complete, the glycine concentration was 66.7 g/l and the NaCl concentration was 151.5 g/l. The resulting precipitate was centrifuged and dissolved, and the activity was measured as for batch 1.

Batch 2a: The remaining supernatant from batch 2 was likewise precipitated further by adding glycine until a glycine concentration of 160 g/l was reached; the precipitate was centrifuged and dissolved, and the activity was measured: (second precipitation)

TABLE 7

Precipitation glycine and NaCl concentrations.

|  | NaCl concentration in the precipitation batch [g/l] | Glycine concentration in the precipitation batch [g/l] |
|---|---|---|
| Batch 1: | 122.2 | 128.3 |
| Second precipitation 1a: | 122.2 | 160.0 |
| Batch 2: | 151.5 | 66.7 |
| Second precipitation 2a: | 151.5 | 160.0 |

Determination of vWF:RcoF, vWF:Ag and FVIII:C gave the following ratio as shown in table 8.

TABLE 8

FVIII:C, vWF:RCoF, vWF:Ag ratios from the batches of example 4.

|  | FVIII:C to vWF:RCoF | FVIII:C to vWF:Ag | vWF:Ag to vWF:RCoF |
|---|---|---|---|
| Batch 1 | 1:2.7 | 1:2.9 | 1:0.9 |
| Second precipitation 1a | 1:10.5 | 1:11.3 | 1:0.9 |
| Batch 2 | 1:2.4 | 1:1.8 | 1:1.3 |
| Second precipitation 2a | 1:2.6 | 1:4.8 | 1:0.6 |

Re table 8: batch 1 and batch 2 showed an advantageous multimer distribution for a vWF concentrate, with even higher representation of high molecular weight multimers in batch 2. The high molecular weight contents were reduced in batch 1a and especially in batch 2a (not depicted).

EXAMPLE 5

Batch A

Production of a Concentrate in which the High Molecular Weight vWF Multimers were Enriched:

As in example 1, 3.64 kg of cryoprecipitate were processed to about 4 000 ml of a diluted pasteurized solution containing vWF and FVIII:C.

Procedure for Precipitation to Give a Fraction with Enriched High Molecular Weight vWF Multimers and FVIII:C:

3 000 ml of a precipitating medium (24.44 g NaCl, 24.15 g glycine, 2 000 ml WFI, pH 6.8) were added over the course of 60 min while stirring to 4 000 ml of the pasteurized, diluted vWF/FVIII:C solution, and incubation was continued without stirring for 90 min. The precipitate which had formed was centrifuged in a centrifuge at 6 000×g for 45 min. The precipitate obtained (precipitate 1) was dissolved ad 400 ml with dissolving buffer (dissolving buffer: 1.46 g NaCl, 10.14 g glycine, 500 ml WFI, pH 7.0).

Stabilization, Final Formulation, Lyophilization

The resulting solution with the enriched high molecular weight vWF multimers was stabilized with 0.5% human albumin and dialyzed to a buffer content of 3.5 g/l NaCl, 5.8 g/l tri-Na citrate×2H$_2$O, 20 g/l glycine, pH 7.0. Dialysis was followed by ultracentrifugation of the solution at 30 000×g for 60 min. The supernatant after ultracentrifugation was decanted. The ultra-centrifuged solution was then divided into part I and part II.

Part I was sterilized by filtration, bottled and lyophilized.

Part II was left as it was and likewise bottled and lyophilized. It is known that microbes are mostly removed during high-speed ultracentrifugation. The purpose of the division was to investigate the effects of sterilization by filtration on the ratio, and whether the spectrum of high molecular weight multimers remains unchanged after sterilization by filtration.

As shown in table 9 hereinafter, the ratio, and thus also the high molecular weight multimer spectrum, was maintained apart from a slight product dilution and a handling loss.

Lyophilization and reconstitution with WFI afforded a concentrate which had a higher vWF:RCoF concentration compared with vWF:Ag. This was attributable to the relatively high content of high molecular weight vWF multimers and represents a particular advantage in the indication of vW syndrome.

Batch B

Production of a Fraction of vWF/FVIII:C-containing Concentrate in which the High Molecular Weight Multimers were Reduced:

The predominantly low molecular weight multimer fraction was obtained from a further preparation batch at a later time (batch B and referred to as precipitate 2).

As in example 1, 3.64 kg of cryoprecipitate were processed to about 4 000 ml of a diluted pasteurized solution which contained vWF and FVIII:C. The precipitation was carried out to give a fraction with reduced high molecular weight vWF multimers and FVIII:C.

3 000 ml of a precipitating medium (350 g NaCl, 165.1 g glycine, 1 000 ml, WFI, pH 6.8) were added over the course of 60 min to 4 000 ml of the pasteurized, diluted vWF/FVIII:C solution while stirring, and incubation was continued without stirring for 90 min. The precipitate which formed was centrifuged in a centrifuge at 6 000×g for 45 min. The precipitate obtained was dissolved in dissolving buffer (dissolving buffer: 1.46 g NaCl, 10.14 g glycine, 500 ml WFI, pH 7.0) ad 400 ml.

This fraction is virtually identical to precipitate 1 from batch A and was deep frozen until used further, and the supernatant obtained from this batch served to obtain the low molecular weight vWF multimer fraction.

The supernatant was precipitated further by increasing the glycine concentration:

About 40 l of supernatant were precipitated by further addition of 30 g/l glycine over the course of 60 min at 25±2° C. with stirring and further incubation without stirring for 60 min. The final concentrations in the batch were 122 g/l NaCl and 158 g/l glycine. The precipitate which formed was centrifuged in a centrifuge at 6 000×g for 60 min. The precipitate thus obtained (precipitate 2) was dissolved in dissolving buffer (dissolving buffer: 1.46 g NaCl, 10.14 g glycine, 500 ml WFI, pH 7.0) ad 250 ml. The supernatant was discarded.

The resulting solution with the reduced content of high molecular weight vWF multimers was stabilized with 0.5% human albumin and dialyzed to a buffer content of 3.5 g/l NaCl, 5.8 g/l tri-Na citrate×2H$_2$O, 20 g/l glycine, pH 7.0.

Dialysis was followed by ultracentrifugation of the solution at 30 000×g for 60 min. The supernatant after ultracentrifugation was decanted, sterilized by filtration and bottled.

Lyophilization and reconstitution with WFI afforded a concentrate which had a lower vWF:RCoF concentration compared with vWF:Ag.

TABLE 9

Activities/ratios in the reconstituted concentrations of example 5.

| | Activities | | |
|---|---|---|---|
| | FVIII:C [IU/ml] | vWF:RCoF [IU/ml] | vWF:Ag [IU/ml] |
| Precipitate 1 part I | 25.1 | 75.0 | 26.1 |
| Precipitate 1 part II | 35.7 | 93.0 | 34.2 |
| Precipitate 2 | 12.8 | 60.5 | 63.8 |

| | Ratios | | |
|---|---|---|---|
| | FVIII:C to vWF:RCoF | FVIII:C to vWF:Ag | vWF:Ag to vWF:RCoF |
| Precipitate 1 part I | 1:3.0 | 1:1.0 | 1:2.9 |
| Precipitate 1 part II | 1:2.4 | 1:1.0 | 1:2.7 |
| Precipitate 2 | 1:4.7 | 1:5.0 | 1:0.9 |

EXAMPLE 6

Plasma from von Willebrand factor concentrate which contains 78 IU/ml vWF:RCoF, 80 IU/ml vWF:Ag and traces of FVIII:C was added to 200 ml of culture supernatant containing 100 IU of recombinant FVIII:C in each of 3 batches (A, B, C). The culture solution was adjusted to 1.6 g/l NaCl and 124 g/l glycine. 150 ml of precipitating medium of the following glycine/NaCl composition were added to each of the batches and stirred:

| Batch A | 122.2 g/l NaCl | 71.1 g/l glycine |
| Batch B | 122.2 g/l NaCl | 90.4 g/l glycine |
| Batch C | 122.2 g/l NaCl | 109.6 g/l glycine |

The precipitate formed was centrifuged in the centrifuge at 30 000×g for 60 min. The precipitate obtained was dissolved in dissolving buffer (dissolving buffer: 1.46 g NaCl, 10.14 g glycine, 500 ml WFI, pH 7.0) and analyzed.

It was observable in this case too that mainly high molecular weight multimers with FVIII:C activity precipitate first at an identical NaCl content and low glycine concentration.

It was evident from this that a partitioning of the vWF multimers according to size can be achieved by appropriate adjustment of the equilibrium with NaCl and glycine also in the culture supernatant which may contain both recombinant FVIII:C and plasma vWF.

LIST OF REFERENCES

1. "Multicenter Comparison of von-Willebrand-Factor Multimer Sizing Techniques". Thrombosis and Haemostasis, F. K. Schattauer Verlag GmbH (Stuttgart) 54 (4) 873-877 (1985).
2. "Electroblot and Immunoperoxidase Staining for rapid Screening of the Abnormalities of the multimeric Structure of von-Willebrand-Factor in von-Willebrand's Disease". Thrombosis and Haemostasis, F. K. Schattauer Verlag GmbH (Stuttgart) 55 (2) 246-249 (1986).
3. "Multimeric Analysis of von-Willebrand-Factor by vertical Sodiumdodecylsulphate Agarose Gelelectro-phoresis, Vacuumblotting Technology and sensitive Visualisation by Alkaline Phosphatase Anti-Alkaline Phosphatase Complex". Thrombosis Research 66, 745-755 (1992).
4. "Structure-Function Relationship of Human von Willebrand Factor". Blood, Vol. 70 No. 3 (September), pp 605-611 (1987).
5. Fass D. N.: "Factor VIII Structure and Function", Ann NY Acad. Sci 614, 76 (1991).
6. Hamer R. J., Koedam J. A., Beeser Visser N H, Bertina R. M., van Mourik J. A., Sixma J. J.: "Factor VIII binds to vWF via its M 80.000 light chain". Eur. J. Biochem., 166, 37 (1987).
7. Cornu P., Larrieu M., Caen J., Bernard J.: "Transfusion Studies in vWF: Effect of bleeding Time and Factor VIII". Br. J. Haematol. 9, 189 (1963).
8. Weiss H. J., Sussmann D., Hoyer L. W.: "Stabilisation of Factor VIII in Plasma by the vWF. Studies of posttransfusion and dissociated Factor VIII in Patients with von-Willebrand's disease". J. clin. invest. 60, 390 (1977).
9. "Synthesis of von-Willebrand-Factor by cultured human endothelial Cells", Proc Natl. Acad Sci USA 71; 1906 (1974).
10. "Synthesis of Factor VIII antigen by cultured Guinea Pig Megakaryocytes", J. clin. invest. 60, 914 (1977).
11. "Therapy of von-Willebrand Disease". Seminars in Thrombosis and Hemostasis, Volume 19, No. 1 (1993).
12. Perret B. A., Furlan M., Beck E. A.: "Isolation of small molecular forms of FVIII/vWF from plasma" Haemostasis 14, pp 289-295 (1984).
13. European patent application EP 0 705 846 A1.
14. A More Uniform Measurement of Factor VIII Inhibitor Thrombos. Diathes. haemorrh. (Stuttg.), 1975, 34, 869
15. Von Willebrand Factor Modulates Factor VIII Immunogenicity:
   Comparative Study of Different Factor VIII Concentrates in a Haemophilia A Mouse Model Thromb Haemost 2002; 88: 221-9 Mathias Behrmann, John Pasi, Jean-Marie R. Saint Remy, Ronald Kotitschke, Michael Kloft

The invention claimed is:

1. A process for producing a concentrate of a factor VIII:C-containing von Willebrand factor (vWF/FVIII:C), comprising subjecting a liquid comprising factor VIII:C (FVIII:C) and von Willebrand factor (vWF) to a fractional precipitation using an effective amount of at least one of an alkali metal salt or an alkaline earth metal salt, and an amino acid chosen from glycine, α- or β-alanine, α- or β- or γ-aminobutyric acid, lysine, valine, asparagine, and glutamic acid, wherein the fractional concentration of the amino acid is from about 67 to about 110 g/l, such that the produced concentrate has an increased content of high molecular weight multimers of vWF, and a ratio of von Willebrand factor ristocetin cofactor activity (vWF:RCoF) to von Willebrand factor antigen (vWF:Ag) of greater than 1.

2. The process as claimed in claim 1 wherein the amino acid is glycine.

3. The process as claimed in claim 1 wherein the alkali metal salt is NaCl.

4. The process as claimed in claim 1 further comprising:
   stabilizing the concentrate product produced during said process with at least one of sucrose, glycine, calcium ions, and albumin; and
   pasteurizing said concentrate product produced during said process.

5. The process as claimed in claim 4, wherein calcium ions are added to stabilize the concentrate product.

6. The process as claimed in claim 1, further comprising prior to the fractional precipitation:

(a) mixing the liquid with an aluminum hydroxide suspension, stirring, and removing the prothrombin complex;
(b) precipitating fibrinogen with an amino acid chosen from glycine, α- or β-alanine, α-, β-, or γ-aminobutyric acid, lysine, valine, asparagine, and glutamic acid and removing said fibrinogen; and
(c) precipitating the vWF/FVIII:C complex using an alkali metal salt or an alkaline earth metal salt.

7. The process as claimed in claim 6, wherein the liquid is human plasma, a plasma fraction, or genetically modified cell material.

8. The process as claimed in claim 7, wherein the plasma fraction is cryoprecipitate.

9. The process as claimed in claim 6, wherein the amino acid is glycine.

10. The process as claimed in claim 6, wherein the alkali metal salt is NaCl.

11. The process as claimed in claim 1, wherein the fractional concentration of the alkali metal or the alkaline earth metal salt is from 100 to 160 g/l.

* * * * *